United States Patent
Lenz et al.

(10) Patent No.: US 6,853,448 B2
(45) Date of Patent: Feb. 8, 2005

(54) MULTI-DIRECTIONAL MIRROR DEVICE AND METHOD FOR OPTICAL INSPECTION AND AUTOFOCUS MEASUREMENT OF OBJECTS

(76) Inventors: Karl J. Lenz, 90 Kaiser-Friedrich-Ring, 65185 Wiesbaden (DE); Albert G. Choate, 348 Honeoye Falls #6 Rd., Rush, NY (US) 14543

(*) Notice: Subject to any disclaimer, the term of this patent is extended or adjusted under 35 U.S.C. 154(b) by 0 days.

(21) Appl. No.: 10/175,531

(22) Filed: Jun. 14, 2002

(65) Prior Publication Data

US 2003/0231316 A1 Dec. 18, 2003

(51) Int. Cl.$^7$ .............................................. G01N 21/00
(52) U.S. Cl. ............................... 356/241.1; 356/237.1; 250/201.2
(58) Field of Search ......................... 356/241.1–241.6, 356/237.1–237.5; 359/385, 390, 798, 882, 503, 802; 250/201.1–201.4

(56) References Cited

U.S. PATENT DOCUMENTS

| | | | | |
|---|---|---|---|---|
| 1,292,326 A | * | 1/1919 | Jacobson | 359/503 |
| 3,761,186 A | * | 9/1973 | Wason | 356/241.1 |
| 4,279,513 A | * | 7/1981 | Tucker | 356/639 |
| 4,440,496 A | * | 4/1984 | Milana | 356/241.1 |
| 4,629,425 A | * | 12/1986 | Detsch | 433/31 |
| 4,714,327 A | * | 12/1987 | Marshall | 359/364 |
| 5,132,837 A | * | 7/1992 | Kitajima | 359/374 |
| 5,253,106 A | * | 10/1993 | Hazard | 359/368 |
| 5,253,638 A | * | 10/1993 | Tamburrino et al. | 600/170 |
| 5,317,387 A | * | 5/1994 | Van Hengel et al. | 356/625 |
| 5,369,491 A | * | 11/1994 | Schneider | 356/626 |
| 5,389,774 A | * | 2/1995 | Gelman et al. | 250/201.1 |
| 5,668,665 A | * | 9/1997 | Choate | 359/663 |
| 5,832,107 A | * | 11/1998 | Choate | 382/154 |
| 6,172,804 B1 | * | 1/2001 | Schuck et al. | 359/384 |
| 6,179,439 B1 | * | 1/2001 | Choate | 362/247 |

* cited by examiner

*Primary Examiner*—Hoa Q. Pham
(74) *Attorney, Agent, or Firm*—Shlesinger & Fitzsimmons

(57) ABSTRACT

The upper end of an elongate, rigid, mirror supporting arm is releasably secured at its upper end to an orientation ring, which is removably and rotatably mounted on the lower, cylindrically shaped end of the objective lens housing of an optical autofocus measurement system. The arm extends at its lower end beneath the housing and has secured thereon a mirror which is spaced beneath the housing, and lies in a plane that intersects and is inclined relative to the optical axis of the optical system contained in the housing. The mirror faces the surface of an object disposed in an object plane spaced laterally from the optical axis of the lens system, so that the system is focused along a supplemental optical axis which is inclined to, and intersects, the optical axis of the system in the housing. Images of the object in the offset object plane are therefore projected along the supplemental axis and then from the mirror to the optical system along its optical axis. This system enables a method of effecting autofocus measurements of an object placed in a first object plane that is intersected by the system optical axis when the mirror arm is removed from the lens housing, and, which also enables autofocusing of object surfaces in a second object plane when the mirror is attached by the arm to the lens housing.

21 Claims, 1 Drawing Sheet

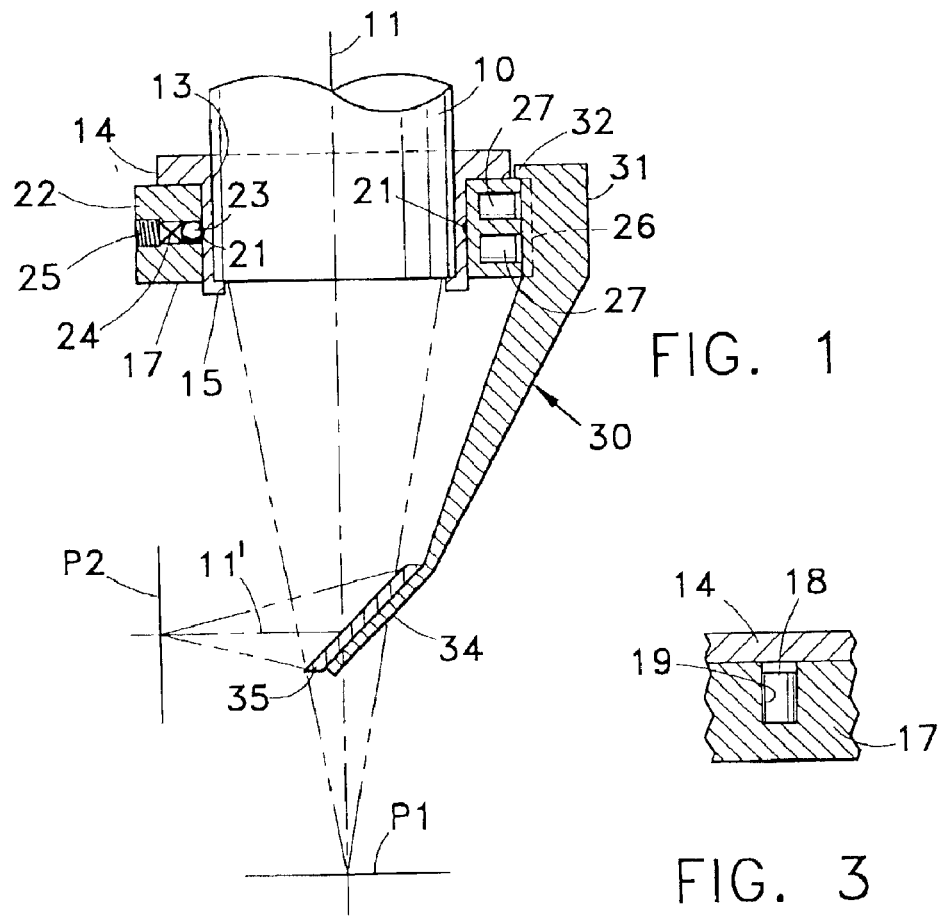
FIG. 1
FIG. 3
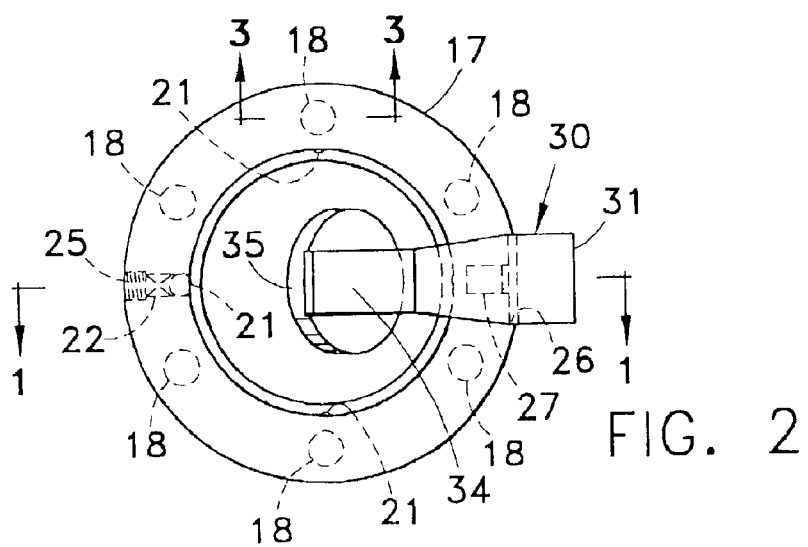
FIG. 2

MULTI-DIRECTIONAL MIRROR DEVICE AND METHOD FOR OPTICAL INSPECTION AND AUTOFOCUS MEASUREMENT OF OBJECTS

BACKGROUND OF THE INVENTION

This invention relates to a device for illuminating and observing various surfaces of a workpiece that are to be subjected to autofocus and video inspection apparatus for accurate measurement of such surfaces. More particularly, this invention relates to a novel multi-directional mirror device and method for effecting inspection and autofocus measurement of selected surfaces of a workpiece.

There are currently available in the marketplace apparatus of various designs for illuminating and effecting accurate measurement of various surfaces of a manufactured workpiece. Typical such apparatus includes a precision optical inspection system for directing illumination downwardly onto an inspected object placed on a horizontal transparent stage. The imaging optics of such apparatus, for example the objective lens or its housing, can be moved vertically to achieve focus, while the stage or work support can be shifted laterally in intersecting X and Y directions to permit observation of different surfaces of the work being inspected. A substage illuminator can be employed beneath the transparent stage to project a silhouette or shadow of the object's features for inspecting still other surface features of the work. The U.S. Pat. Nos. 5,832,107, 5,668,665, and U.S. Pat. No. 5,389,774 disclose various such systems for directing illumination downwardly through an objective lens or lens housing onto a workpiece for purposes of inspecting and effecting measurements of various surfaces thereof. Still other illuminating apparatus, such as disclosed for example in U.S. Pat. No. 6,179,439 have been employed with such inspection apparatus in order to direct illumination laterally onto side surfaces of the workpiece that is being inspected.

However, in order to view an object from different directions by inspection apparatus of the type noted above, it is necessary for the inspected object to be manipulated so as to present alternative views to the inspection lens system. Typically this manipulation can be accomplished manually or by using grippers and rotary axes to reorient the position of the object. To avoid the necessity of manipulating the object, it is conceivable that a more complex system might incorporate multiple optical systems for viewing an object from different directions simultaneously. Also while it has been proposed to employ an adjustable or a swiveling observation tube or lens as disclosed for example in U.S. Pat. No. 6,172,804, such devices can be expensive to manufacture and to incorporate into inspection apparatus of the type described. To avoid such problems, some optical systems which are designed with sufficient working distance—i.e., clearance between the optics and the inspected object, have sometimes employed mirrors to provide views of the object's sides from above. However, such mirrors are typically secured or held upon the XY supporting stage, and are not capable of viewing inside surfaces such as the internal walls of an open box or an inner surface of a cylinder.

It is an object of this invention, therefore, to provide for autofocus measurement equipment a novel multi-directional mirror device which is releasably attached to and adjustable relative to the inspecting optics selectively to direct a variety of different images to the system optics.

A more specific object of this invention is to provide any one of a number of different, replaceable mirrors each of which is disposed to be releasably mounted on and suspended beneath the objective lens housing of inspection apparatus to be disposed in a plane inclined to and extending transversely of the optical axis of the apparatus, thereby to project the imaging optical axis at some angle to the vertical, and for rotation selectively into different angular of positions about the optical axis.

It is an object also of this invention to provide a novel method of inspecting and effecting autofocus measurements of various surfaces of a workpiece along intersecting optical axes.

Still other objects of this invention will be apparent hereinafter from the specification and from the recital of the appended claims, particularly when read in conjunction with the accompanying drawings.

SUMMARY OF THE INVENTION

Secured coaxiallly to the lower end of the objective lens housing of an optical inspection and autofocus measurement system is a metal collar having on its upper end an enlarged diameter, circumferential flange. Removably secured by magnets beneath the flange and for rotatable adjustment into different positions of rest about the collar is an orientation ring. Removably secured at its upper end by other magnets to the orientation ring, and extending at its lower end beneath the objective lens housing is a rigid arm carrying a reflective surface lying in a plane that intersects and is inclined to the optical axis of the system's objective lens. The system can then focus (and autofocus) along a supplemental optical axis on surfaces lying in an object plane (e.g. vertical) different from the object plane (e.g. horizontal) upon which the system is normally designed to focus. This multi-directional mirror device has the further advantage of providing a novel method of using a conventional optical inspection and autofocus measuring system for securing various measurements of the surfaces of objects, or different portions of the same object, which lie in different object planes. Measurements are made in one object plane without use of the mirror device, and in a different object plane by using the device with a conventional optical inspection system.

THE DRAWINGS

FIG. 1 is a fragmentary side view of a multi-directional mirror device made according to one embodiment of this invention, portions of the mounting collar and orientation ring of the device being shown in section, as taken along the line 1—1 in FIG. 2 looking in the direction of the arrows;

FIG. 2 is a bottom plan view of this device; and

FIG. 3 is a fragmentary sectional view of the orientation ring taken along the lines 3—3 in FIG. 2 and looking in the direction of the arrows.

DETAILED DESCRIPTION OF THE PREFERRED EMBODIMENTS

Referring now to the drawing by numerals of reference, 10 denotes the cylindrically shaped lower end of a lens housing or barrel containing the objective lens of an optical system of the type such as disclosed for example in U.S. Pat. Nos. 4,743,771 and 5,668,665. Such system is designed to inspect objects positioned beneath the lower end of the housing 10 for illumination by light emanating from housing 10 and/or some other source, and is capable of conducting autofocus range measurements. The optical axis 11 of the optical system in housing 10 is disposed at right angles to the object plane P1, which is the plane for which the optical system in housing 10 is originally designed.

However, to enable the optical system in housing 10 to be employed for observing objects in a different object plane, for example plane P2 in FIG. 1, the lower end of lens housing 10 is modified by having secured coaxially thereabout a metallic,tubular mounting collar 13. At its upper end collar 13 has integral therewith and projecting radially outwardly therefrom, a rather large, circumferential metal flange 14, which is disposed coaxially about housing 10. On its lower end collar 13 has integral therewith, and projecting radially inwardly therefrom, a rather small, circumferential flange 15, the upper surface of which overlies a marginal circumferential portion of the lower end of housing 10.

Mounted for rotational adjustment coaxially about the mounting collar 13 beneath its circumferential flange 14 is a circular, orientation ring 17, which is rectangular in cross section, and which has its upper surface slidably engaged with the underside of the circumferential flange 14, and its inner peripheral surface disposed in slidable engagement with the outer peripheral surface of the collar 13. Ring 17 is mounted both rotatably and removably against the underside of flange 14 by a plurality of like, generally disc-shaped magnets 18 (six in the embodiment illustrated), which are secured or otherwise embedded in six openings or recesses 19 which are formed in the upper surface of the ring 17 at 30° intervals about its axis. The magnetic poles of the magnets 18 confront upon the underside of the flange 14 and removably and rotatably retain the orientation ring 17 in any one of a number of different angular positions, as noted in greater detail hereinafter.

Intermediate its ends the mounting collar 13 has formed in its outer peripheral surface a plurality (four in the embodiment illustrated) of small, segmental-conical recesses 21 which are arranged at 90° intervals about the axis of the collar. Substantially medially of its ends (the upper and lower ends as shown in FIG. 1) the orientation ring 17 has therethrough a radially extending opening 22 having moveably mounted at its inner end a spherically shaped ball detent 23, intermediate its ends a small, coiled compression spring 24, and in its outer end a small set screw 25 which is threaded into the outer end of opening 22 to maintain the spring 24 in slightly compressed condition between the detent 23 and the set screw 25. In practice, the detent 23 is urged by the spring 24 into rolling or sliding engagement with the outer peripheral surface of collar 13, and is designed to be releasably seated in any one of the four recesses 21 in the outer surface of collar 13. Thus the orientation ring 17 can be rotated, manually or otherwise, and into any one of four different angular positions about the optical axis 11.

Medially of the angular space between an adjacent pair of the mounting magnets 18 the orientation ring 17 has formed in its outer peripheral surface a rectangular recess or notch 26. Secured in a pair of axially spaced circular openings formed in the orientation ring 17 radially thereof to open on the bottom of its notch 26 are two, like, circular magnets 27, the magnetic ends or poles of which confront upon the recess 26. Removably mounted at its upper end on ring 17 for adjustment thereby about the optical axis 11 is an elongate mirror supporting arm, which is denoted generally by the numeral 30. Arm 30, which is made from a magnetizable ferrous material, has a generally rectangularly shaped upper end 31 one side of which is seated in the rectangular notch 26 in the outer surface of ring 17, and in such manner that a planar surface on the end 31 of the arm is releasably secured magnetically to the ring 17 by the magnets 27. To assist in retaining the arm 30 on ring 17 for adjustment thereby, a marginal portion or integral lip section 32 of the arm 30 overlies the upper surface of ring 17 at the bottom of its notch 26.

The lower end of the arm 30 has formed thereon a generally planar mirror supporting section 34 disposed in a plane inclined at 45° to the optical axis 11, with the lower edge thereof just intersecting axis 11. Secured on the upper surface of section 34 of the arm 30 is the planar, rear surface of an eliptically shaped mirror, the opposite or upper, reflective surface thereof also lying in a plane which intersects the optical axis 11 at 45°. Referring to FIG. 1, P1 denotes the original object plane, or the plane upon which the optical system in housing 10 normally can be expected to be focused. However, because of the presence of the eliptical reflective surface of the mirror 35, which is disposed in a plane at 45° to the optical axis, the optical system in housing 10 is instead focused along a supplemental optical axis 11' upon a diverted object plane P2 in FIG. 1, which happens to be at right angles to the object plane P1. This enables inspection and measurement of vertical surfaces such as the inner and outer surfaces of a cylinder or other workpiece having inner and outer surfaces that are to be inspected. Various portions of such surfaces can be viewed simply by rotating ring 17, and hence the arm 30, then into any one of the four different angular positions about the optical axis 11 in each of which the ring 17 and hence arm 30 will be releasably secured by engagement of the spring loaded ball detent 21 with one of the four recesses 21 in collar 13. If desired, the arm 30 can be removed from ring 17 simply by withdrawing the upper end 31 of the arm 30 from the notch 26 in ring 17, simply by overcoming the magnetic attraction of the magnets 27. Thereafter the lens housing 10 can be vertically adjusted to achieve the desired focus on the surface or different surfaces of an object or workpiece located in the object plane P1.

A particular advantage of the use of the adjustable arm 30 is that it permits a novel method of procuring autofocus measurement of surfaces of an inspected object, which lie in different object planes, by manipulation of the optical axis of autofocus measurement equipment of the type referred to in the above-noted U.S. Pat. No. 4,743,771 and U.S. Pat. No. 5,668,665. Such prior art involve the use of optical systems in which the respective objective lens assembly is disposed in a housing that permits inspection of only those surfaces of an object disposed in a first object plane (typically horizontal) and which are intersected by the system's optical axis, and which permits the system's objective lens to be adjusted for focusing purposes solely with respect to the system's optical axis. Autofocus measurement, therefore, can be effected only in connection with object surfaces which are intersected by the optical axis of the system. As a result of employing the equipment disclosed herein, it is now possible for such conventional apparatus to be modified to enable a system's optical axis to be focused upon a reflective surface inclined to the system's optical axis so that a supplemental optical axis, which is inclined to the system's optical axis, can now be directed upon object surfaces other than those that are intersected by the system axis, and which, lie in an object plane different from the above-noted first object plane. Thus, upon vertical movement of the optical system along the system's optical axis, the images received by the optical system via the supplemental optical axis will be autofocusable images not heretofore observable by conventional systems of the type in which object surfaces can be observed only when intersected by the system optical axis.

From the foregoing, it will be apparent that the present invention provides a relatively simple and inexpensive means for selectively supplementing a conventional optical inspection device so that the device can be employed not only to focus upon the upper surfaces of an object placed in an object plane immediately beneath the system's objective lens, but also can be selectively supplemented with a mirror arm and associated orientation ring for permitting inspection and autofocus measurement of object surfaces placed in an object plane disposed in laterally offset spaced relation to the optical axis of the optical inspection system. With the mirror arm being rotatably adjustable into a variety of different angular positions about the optical axis 11, the optical system can be subjected to a variety of different views without having to manipulate or adjust the object that is being inspected. By employing the magnets 27 for releasably supporting the mirror supporting arm on the orientation ring 17, considerable amount of time and effort is saved whenever it is desirable to remove or remount the arm 30 onto ring 17. Moreover, should lateral movement of the housing 10 accidentally cause the arm 34 to be engaged with the stationary surface, the arm 30 will simply be disconnected from ring 17 without causing any damage to the arm or its mirror 35. The magnets 18 also simplify the mounting of the ring 17 onto, or its removal from, the mounting collar 13.

While this invention has been illustrated and described in detail in connection with only certain embodiments thereof, it will be apparent that it is capable of still further modification, such as for example employing modifications of holder 30 which support the reflective surfaces of their mirrors 35 to intersect the optical axis at angles other than 45°. In such cases it would be possible also to employ arms 30 which employ mirrors of different sizes, as well as different inclination angles relative to the optical axis and different distances from the objective lens in housing 10. It will be apparent also that this application is intended to cover any such modifications as may fall within the scope of one skilled in the art or the appended claims.

What is claimed is:

1. In combination with an optical inspection system having an objective lens housing one end of which is position to overlie and direct the system's optical axis onto a first object plane, a multi-directional mirror device, comprising
   an elongate arm,
   mounting means securing one end of said arm removably to said one end of said housing and for rotation about said one end coaxially of said optical axis, and
   said arm extending at its opposite end beneath said one end of said housing and having secured thereon a mirror the reflective surface of which faces said one end of said housing and lies in a plane extending transversely of said optical axis.

2. The combination as defined in claim 1, wherein said plane is inclined at 45° to said optical axis.

3. The combination as defined in claim 1, wherein said reflective surface is elliptical in configuration and is centered on said optical axis.

4. The combination as defined in claim 1, wherein said reflective surface is operatice to focus said optical system on a second object plane extending transversely of said first object plane.

5. The combination as defined in claim 1, wherein said mounting means comprises, an orientation ring removably mounted on said one end of said housing for rotation thereabout coaxially of said optical axis and selectively into any one of a plurality of different positions of rest equiangularly spaced about said axis, and
   means releasably securing said one end of said arm to said ring for rotation therewith.

6. The combination as defined in claim 5, wherein
   said one end of said arm is made of ferrous metal, and
   said means releasably securing said one end of said arm to said ring comprises at least one magnet secured in said ring in registry with and magnetically coupled to said one end of said arm.

7. The combination as defined in claim 5, wherein said mounting means further comprises,
   an annular collar secured to and surrounding said one end of said housing coaxially of said orientation ring,
   said collar having in its outer peripheral surface a plurality of like recesses angularly spaced from each other about the axis of said collar, and
   a spring-loaded detent mounted in said ring and projecting from the internal peripheral surface thereof releasably to engage in one of said recesses in said collar, whenever said ring is in one of said positions of rest.

8. A method of employing the same optical system for inspecting and measuring surfaces of an object along at least two different optical axes, including
   providing an optical inspection and autofocus measurement system including a housing containing an objective lens assembly the optical axis of which is directed through an opening in said housing to permit focus of said system onto the surface of an object disposed in a first object plane,
   moving said system along said axis to effect autofocus measurements of surfaces of said object in said first object plane,
   removably positioning a reflective surface in an operative position in the space between said housing and said first object plane, said reflective surface confronting said opening in said housing and lying in a plane and inclined to and intersecting said optical axis of said objective lens assembly, and
   moving said system and said reflective surface along the optical axis of said lens assembly when said reflective surface is in said operative position thereby to effect autofocus measurements of surfaces of said object in a second object plane.

9. A method as defined in claim 8, including, rotatably adjusting said reflective surface about the optical axis of said assembly into any one of a plurality of different positions of rest corresponding to said operative position.

10. In combination with an optical inspection system having an objective lens housing one end of which is positioned to overlie and direct the system's optical axis onto a first object plane, a multidirectional mirror device, comprising
    an elongate arm,
    an orientation ring removably mounted on said one end of said housing for rotation for rotation thereabout coaxially of said optical axis and selectively into any one of a plurality of different positions or rest spaced about said axis,
    said one end of said arm is made of ferrous metal,
    at least one magnet secured in said ring in registry with and magnetically coupled to said one end of said arm to removably secure said arm to said ring, and
    said arm extending at its opposite end beneath said one end of said housing and having secured thereon a mirror the reflective surface of which faces said one end of said housing and lies in a plane extending transversely of said optical axis.

11. The combination as defined in claim 10, and further comprising:
an annular collar secured to and surrounding said one end of said housing and coaxially of said orientation ring, said collar having in its outer peripheral surface a plurality of like recesses angularly spaced from each other about the axis of said collar, and
a spring-loaded detent mounted in said ring and projecting from the internal peripheral surface thereof releasably to engage in one of said recesses in said collar, whenever said ring is in one of said positions of rest.

12. The combination as defined in claim 11, wherein: said recesses are equi-angularly spaced about said axis.

13. An internal surface inspection method comprising: providing an inspection system, including:
providing optics arranged to inspect an object on a stage movable in an x-y plane;
arranging the optics to focus along an optical axis orthogonal to the x-y plane; and
providing a control system in communication with the stage and the optics;
providing a reflective surface between the optics and the object, including deflecting the optical axis by an angle to the optical axis and in a direction in the x-y plane;
moving the deflected optical axis into intersection with an internal surface of the object to be inspected; and
acquiring measurements of at least one of a surface of the object and a property of light reflected from the object.

14. The method of claim 13 wherein providing a mirror comprises:
providing an elongate arm;
mounting an orientation ring removably on one end of the housing for rotation thereabout coaxially of the optical axis and selectively into any one of a plurality of different positions or rest spaced about the axis;
forming the one end of the arm from a ferrous metal;
securing at least one magnet in the orientation ring in registry with and magnetically coupled to the one end of the arm to removably secure the arm to the ring; and
arranging the arm with an opposite end opposite the one end extending beneath the one end of the housing;
securing on the opposite end a mirror with a reflective surface facing the one end of the housing and which lies in a plane extending transversely of the optical axis.

15. The method of claim 13 further comprising employing at least one autofocusing technique to measure a location of at least one of an imaged surface and an object feature along the redirected optical axis.

16. The method of claim 15 wherein the at least one autofocusing technique includes moving the object through a best focus position, analyzing a series of images captured while moving the object through the best focus position, and calculating a location of optimum focus.

17. The method of claim 16 further comprising distance ranging by computation of a zero-crossing of a first derivative of a curve of contrast measured as sum of intensity gradients squared.

18. An internal surface inspection method comprising:
providing an inspection system with a stage movable in an x-y plane and optics focusing along an optical axis substantially orthogonal to the x-y plane;
diverting the optical axis to an interior of an object to be inspected so that an internal surface of the object is intersected by the diverted optical axis, the object to be inspected being supported on the stage;
acquiring a series of images of an internal surface to be inspected while moving the object through a best focus position;
analyzing the series of images to calculate a location of optimum focus; and
reporting the location of optimum focus as a measurement of a location of at least one of an imaged surface and an object feature.

19. The method of claim 18 further comprising:
providing a control system in communication with the stage and the optics; and
acquiring measurements of at least one of a surface of the object and a property of light reflected from the object.

20. The method of claim 18 wherein diverting the optical axis further comprises:
providing a reflective surface between the optics and the object, including deflecting the optical axis by an angle to the optical axis; and
moving the deflected optical axis into intersection with an internal surface of the object to be inspected.

21. The method of claim 19 wherein providing a reflective surface comprises:
providing an elongate arm with first and second ends opposite one another on the arm, including forming the first end from a ferrous material;
mounting an orientation ring removably on an end of the housing for rotation thereabout coaxially of the optical axis and selectively into any one of a plurality of different positions or rest spaced about the axis;
securing at least one magnet in the orientation ring in registry with and magnetically coupled to the first end of the arm to removably secure the arm to the ring; and
arranging the arm with the second end extending beneath the end of the housing;
securing on the second end a mirror with a reflective surface facing the one end of the housing and which lies in a plane extending transversely of the optical axis.

* * * * *